(12) United States Patent
Mikkelsen et al.

(10) Patent No.: US 6,391,577 B1
(45) Date of Patent: May 21, 2002

(54) RAPID ELECTROCHEMICAL ASSAY FOR ANTIBIOTIC AND CYTOTOXIC DRUG SUSCEPTIBILITY IN MICROORGANISMS

(75) Inventors: Susan R. Mikkelsen, 510F Albert Street, Waterloo, Ontario (CA), N2L 3V4; Peter Ertl, Waterloo (CA)

(73) Assignee: Susan R. Mikkelsen, Waterloo (CA)

( * ) Notice: Subject to any disclaimer, the term of this patent is extended or adjusted under 35 U.S.C. 154(b) by 0 days.

(21) Appl. No.: 09/261,195

(22) Filed: Mar. 3, 1999

(51) Int. Cl.[7] .................................................. C12Q 1/18
(52) U.S. Cl. ........................................... 435/32; 435/25
(58) Field of Search ................................ 435/32, 4, 25; 204/403, 431

(56) References Cited

U.S. PATENT DOCUMENTS

| | | |
|---|---|---|
| 3,506,544 A | 4/1970 | Silverman et al. |
| 4,129,483 A | 12/1978 | Bochner |
| 4,209,586 A | 6/1980 | Nöller |
| 4,898,816 A * | 2/1990 | Turner et al. .................. 435/34 |
| 5,045,477 A | 9/1991 | Belly et al. |
| 5,126,034 A * | 6/1992 | Carter et al. ................. 204/403 |
| 5,348,862 A | 9/1994 | Pasero et al. |
| 5,501,959 A * | 3/1996 | Lancaster et al. .............. 435/32 |
| 5,576,481 A | 11/1996 | Beardwood |
| 5,611,900 A | 3/1997 | Worden et al. |
| 5,654,165 A | 8/1997 | Kusunoki et al. |
| 5,792,622 A | 8/1998 | Botsford |
| 5,811,255 A | 9/1998 | Hunter et al. |
| 5,876,959 A * | 3/1999 | Kusunoki et al. ............. 435/34 |
| 6,143,555 A * | 11/2000 | Kusunoki et al. ........ 435/287.1 |

* cited by examiner

Primary Examiner—Ralph Gitomer
(74) Attorney, Agent, or Firm—Kathleen E. Marsman; Borden Ladner Gervais LLP

(57) ABSTRACT

This invention presents rapid methods for evaluating the effects of antimicrobial compounds on microorganisms based upon the microorganism's ability to transport electrons to an external chemical oxidant (a mediator) that is added to the microorganism sample. The mediator interacts with the terminal components of the respiratory pathway and the extent of its consumption is related to the ability of the microorganism to respire. However, under the assay conditions described herein the extent of mediator consumption is different from the microorganisms' ability to consume oxygen, due to the addition of metabolizable compounds to the assay mixtures. The consumed mediator is subsequently measured electrochemically (amperometrically or coulometrically) at the working electrode of a standard two-electrode or three-electrode electrochemical cell. The electrochemical signals (change of current or charge with time) obtained with microorganism suspensions incubated in the absence and presence of antimicrobial compounds are significantly different. These signal differences can be used to screen for antimicrobial effectiveness of antibiotic drugs against clinically important multi-drug-resistant organisms, to screen for the presence of unlawful levels of antibiotic compounds in foodstuffs, or to screen potential new antimicrobial compounds for effectiveness against different species of microorganisms.

16 Claims, 1 Drawing Sheet

RAPID ELECTROCHEMICAL ASSAY FOR ANTIBIOTIC AND CYTOTOXIC DRUG SUSCEPTIBILITY IN MICROORGANISMS

BACKGROUND OF THE INVENTION

Microorganisms are the most diverse and plentiful form of life on Earth. Many species of microorganisms are harmful to animals or humans, and for this reason antimicrobial compounds are given to humans for microbial infections, and to livestock animals as regular food additives. Worldwide overuse of antibiotic compounds is a great concern to health-care providers, because of the relatively recent discovery of the evolution of multi-drug-resistant (MDR) organisms. Many of these MDR organisms are pathogenic: they are harmful and possibly fatal to animals or humans. They have evolved from strains of organisms that had been easily treated with common antibiotic drugs. Rapid new methods for the determination of antimicrobial susceptibility are needed to screen MDR organisms for the effectiveness of a range of antimicrobial compounds, to determine proper treatment of infections. Furthermore, the detection of unlawful levels of antibiotics in animal carcasses and other human foodstuffs are needed in order to minimize the overuse of antibiotics and prevent or minimize the evolution of further MDR organisms.

Methods for the detection of a microorganism's antimicrobial susceptibility are diverse. Most established, commercially-available methods rely on the observation of reproduction (growth) over a relatively long period of time (4 hours to several days) and compare the extents of growth for microorganisms cultivated in the absence and presence of antimicrobial compounds. Effective antimicrobial agents reduce or eliminate growth.

More recently, antibiotic susceptibility testing methods have emerged that are based on the direct visual observation or instrumental measurement of changes in the ability of a microorganism to respire, or breathe, in the presence of an antibiotic or cytotoxic compound.

These methods involve the addition of a special chemical compound or mixture of compounds to the culture of microorganisms (cell culture). After an incubation time, a change in color (light absorption wavelength and/or intensity) or fluorescence (light emission wavelength and/or intensity) is observed, either visually or with an instrument. This change occurs because the microorganism transfers electrons to (reduces) the special chemical compound or mixture of compounds. An early example of this principle is contained in U.S. Pat. No. 4,129,483 (Bochner), in which colorless tetrazolium salts are reduced to colored formazan dyes because of respiration. However, drawbacks include the toxicities and insolubilities of the formazan dyes and their low color intensities (molar absorptivities).

U.S. Pat. No. 5,501,959 (Lancaster et al.) describes an antimicrobial susceptibility test in which the dye resazurin is reduced to resorfurin by microorganisms in the presence of poising agents that control the electrochemical potential of the solution: after time is allowed for the microorganisms to reproduce, the measured rate of resazurin reduction is slower in the presence of antibiotic compounds. Resazurin is deep blue, and nonfluorescent, while the reduction product, resorfurin, is red and highly fluorescent. When effective antibiotic compounds are present, the microorganism does not reproduce to the extent necessary to change the solution color from blue to red. However, in this method, growth of the microorganism is essential to yield the red-colored product, because the microorganisms initially present in the sample are at a very low level and must reproduce in order to be able to generate visual or obvious color changes.

U.S. Pat. No. 5,045,477 (Belly et al.) describes special dye molecules, called "shiftable detectable species", and methods for their use, where reduction causes the chemical release of a colored or fluorescent product which is readily measurable by the absorption or emission of light of a particular wavelength.

U.S. Pat. No. 5,792,622 (Botsford) describes a method for the microbiological assay of chemicals, based on the inhibition of dye reduction that results from exposure to chemicals that are toxic to the microorganism. The dyes described in this patent are tetrazolium salts, that produce formazan dyes when they are reduced by the microorganism. Measurement of the extent of reduction is performed by absorption spectrophotometry.

The methods described above all make use of light absorbance or emission by compounds that are reduced by microorganisms as they respire. The methods cited above are described for use in antibiotic susceptibility assays.

Several examples exist in which electrochemical methods have been used to measure the extent of reduction of a reducible compound that is either naturally present, such as molecular oxygen, or specially added to the cell culture sample, such as a mediator, or mediator mixture. These methods are based on either potential measurement (potentiometric, near zero current) or current measurement (amperometric, fixed applied potential) techniques. The reasons for making these measurements, and the purposes of the methods, are diverse.

In one method, described in U.S. Pat. No. 3,506,544 (Silverman et al.), the objective is to quantitate or measure enzymes, where the term enzyme is clarified to mean purified enzyme preparations, cell-free extracts, and whole cells. The method requires a first substrate (the mediator), an enzyme (to be quantitated) and a second substrate, with which the enzyme, extract or cell reacts. The mediator compounds described are organic compounds including methylene blue, 2,6-dichlorophenolindophenol, phenosafranin, and phenazine methosulfate. The method includes the amperometric measurement of currents produced by oxidation of enzyme-reduced mediator, using a 2-electrode or a 3-electrode electrochemical cell. In one example, cell concentrations are determined by this method for yeast cells (*Saccharomyces cerevisiae*).

U.S. Pat. No. 5,126,034 (Carter et al.) describes a device for the electrochemical quantitation of biological cells. In this device, a filter is used to trap and increase the concentration of microorganisms. Amperometric measurements are made, using p-benzoquinone as a mediator. In one example, the screening of several species of bacteria is reported, and these are *Bacillus badius, Bacillus cerius, Bacillus sphaericus, Bacillus subtilis, Escherichia coli, Pseudomonas fluorescens* and *Salmonella typhimurium*.

U.S. Pat. No. 5,576,481 (Beardwood et al.) describes a method to detect microbial fouling of water and an apparatus to perform the method. In this case, a biofilm caused by microbial fouling grows on an electrode material. The measurement uses linear polarization resistance with an AC method for resistance compensation, in order to measure the corrosion current at the electrode material that is caused by the biofilm. The current is caused by the direct oxidation of the electrode material, and mediators are not used. The corrosion current is converted by calculation into a fouling factor, which is used to determine the extent of water fouling by microorganisms.

U.S. Pat. No. 5,611,900 (Worden et al.) describes devices called microbiosensors that use surface-bound enzymes or microorganisms that are bound to an electrode surface to measure the concentrations of different species that are low molecular weight chemical compounds that the microorganisms are capable of metabolizing, or converting to other chemical compounds. The devices described in this patent all include an amperometric oxygen microelectrode to directly measure dissolved oxygen levels. The surface-bound enzymes or microorganisms must consume oxygen in a dose-dependent manner relating to the concentration of the metabolizable low molecular weight chemical compound, and the purpose of these devices is to measure the concentrations of these metabolizable compounds.

U.S. Pat. No. 5,811,255 (Hunter et al.) describes an apparatus and method for aerobic and anaerobic respiration measurements on microorganisms. The microorganism cultures included are aerobic, denitrifying, sulfate-reducing and/or methanogenic. In this patent, measurement of respiration rates and other parameters of the culture are made using ion-selective electrodes, pH electrodes, oxidation-reduction potential electrodes and an ion chromatograph. The measurements made using electrodes are all potentiometric, and relate a measured voltage to the concentration of a low molecular weight, dissolved chemical compound or to the oxidation-reduction potential of the culture. The purpose of this invention is to provide an apparatus and method to be used to optimize the design of wastewater treatment or bioremediation processes.

None of the preceding electrochemical methods or devices have been used to screen microorganisms for their susceptibility to antimicrobial compounds; however, all include the measurement of microorganism respiration rates.

U.S. Pat. No. 4,209,586 (Noller) describes a method for measuring the effectiveness of growth-inhibiting agents on microorganisms in which a potentiometric measurement is used to measure the oxidation-reduction potential of the microorganism culture over a period of time. The normal change in potential, measured without growth-inhibiting agents present, is approximately constant and moves towards more positive values, but if a growth inhibitor is present, the potential moves towards more negative values. This invention relies on measurement of the potential of the culture medium as the cells grow, and does not measure respiration rates.

U.S. Pat. No. 5,348,862 (Pasero et al.) describes a method for the quantitation of microorganisms in liquids. This method employs a filter to capture and increase the quantity of microorganisms in the sample to be tested, and uses amperometric measurement to quantitate the respiration rate of the sample. The measured current is related to the concentration of microorganisms in the sample. In this example, a mediator is used to transport electrons from the microorganisms to the working electrode to generate the respiration-induced current. Typical mediators used in this method are sodium or potassium ferricyanide or benzoquinone or mixtures thereof. The method consists of a first current measurement in the presence of the filter with bacteria, a second step consisting of rinsing the measurement cell and treating the filter with a biocidal liquid to kill bacteria, and a third step consisting of a second current measurement in the presence of the treated filter. Current values observed in the third step are subtracted from current values observed in the first step, and the difference is used to measure the concentration of microorganisms. The biocidal liquids described are solutions of sodium hypochlorite, formaldehyde and chlorine dioxide.

U.S. Pat. No. 5,654,165 (Kusunoki et al.) describes an apparatus and method for screening antibacterial drugs against aerobic microorganisms that normally consume oxygen as they respire. In this case, a test microorganism is added to a solution that contains the antibacterial drug and one that does not contain the drug. Sensitivity of the microorganism to the drug is determined by measuring the resulting concentration of dissolved oxygen in the two solutions using two amperometric oxygen electrodes. Sensitivity to the antibacterial drug is indicated if the two amperometric oxygen electrodes measure different concentrations of dissolved oxygen. Two strains of *Escherichia coli* as well as *Staphylococcus aureus, Kliebsiella pneumoniae* and *Pseudomonas aeruginosa* were used as examples, and the antibiotic drugs that were screened were ampicillin, streptomycin, chloramphenicol, tetracycline and sulfanilamide. This apparatus and method are restricted to the screening of aerobic microorganisms, because oxygen consumption is measured.

SUMMARY OF THE INVENTION

This invention provides a rapid new method to be used either for the determination of antibiotic or cytotoxic susceptibility in microorganisms, or for the determination of the presence or absence of antibiotic or cytotoxic compounds in samples using microorganisms with known susceptibilities.

The method for assessing susceptibility of a microorganism to an antibiotic or cytotoxic drug comprises adding a suitable mediator or mediator mixture to a sample of the microorganism in the presence of the drug, and assessing variation of the microorganism's respiration rate overtime by electrochemical measurement of mediator consumption resulting from microorganism respiration. This is compared with variation of the respiration rate of another sample of the microorganism not exposed to the drug.

The preferred method further comprises a sample preparation step, in which the cell culture or suspension of microorganisms is combined with a solution of the proposed antibiotic or cytotoxic drug and incubated for a fixed time, a second step in which a mediator or mediator mixture is added, and a third step in which an amperometric or coulometric measurement is made at fixed applied potential, using standard, commercially available electrochemical instrumentation (a potentiostat) and either a 2-electrode or a 3-electrode electrochemical cell. The first two steps can be combined into one step in some embodiments. In the absence of antimicrobial compounds, the mediator is converted by the microorganism from the oxidized to the reduced form at a rate that is characteristic of the organism and the concentrations of organism and mediator in the sample. During the measurement step, the reduced mediator is reconverted to the oxidized form at the working electrode by applying a fixed voltage to the working electrode, relative to a reference or counter electrode, and the magnitude of the measured current is proportional to reduced mediator concentration in the sample. When effective antimicrobial compounds are present during the incubation and measurement steps, the rate of mediator reduction, and the resulting measured signals, are significantly different and are usually much lower than the rate measured in the absence of the antimicrobial compound.

The preferred method for the determination the presence or absence of antibiotic or cytotoxic compounds in a sample comprises adding to the sample a microorganism with known susceptibilities and a suitable mediator or mediator mixture, and assessing variation of the microorganism's respiration rate over time by electrochemical measurement of mediator consumption resulting from microorganism respiration. This rate is compared with variation of the respiration rate of another sample not exposed to such compounds.

The mediator or mediator mixture can be any suitable oxidant, including for example one or more of the following:
- ferricyanide (hexacyanoferrate (III) is another name for this);
- dichlorophenol-indophenol (DCIP);
- ferrocene and ferrocene derivatives;
- methylene blue;
- janus green;
- tris(bipyridyl)iron (III);
- the quinone class which includes benzoquinone, naphthoquinone, menadione, anthraquinone, and substituted derivatives of these; and
- the phenazine class which includes phenazine methosulfate and phenazine ethosulfate.

DETAILED DESCRIPTION OF THE INVENTION

Figure 1:
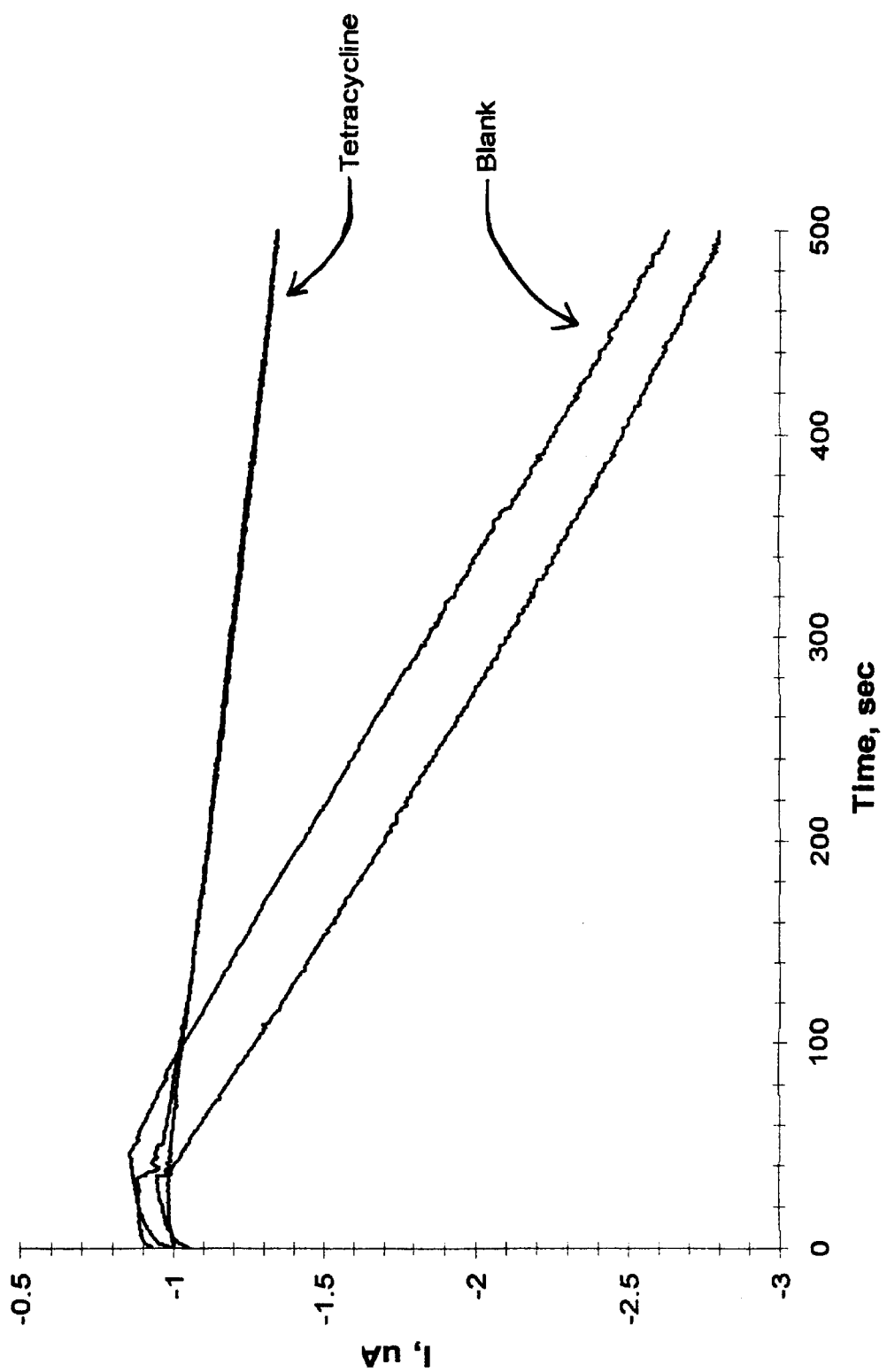
FIG. 1 shows plots of measured current against time for *E. coli* samples from Example 1. The potential of the platinum electrode (area=0.50 cm$^2$) is fixed at +0.50 V vs. Ag/AgCl reference electrode. Traces shown in (a) were obtained in the absence, and in (b) in the presence of 5.1 mM tetracycline.

The invention is based on the measurement of respiration (breathing) rates in microorganisms. Under natural conditions, microorganisms consume molecular oxygen (if they are aerobic) or another oxidant (if they are anaerobic). With aerobic organisms, oxygen is converted to water by proteins present in the membranes of the organisms. The oxygen is transformed by a process known as reduction, in which four protons and four electrons are supplied from the interior of the cell, causing the conversion of oxygen to water. This process can be made to occur with other oxidants, or mediators, that can also accept electrons (with or without protons) from the cell. This invention uses mediators that can accept electrons from the cells and transfer them to a conducting, amperometric electrode, to generate a current that is measured. The electrodes and measuring equipment used in the invention are commercially-available and well-characterized.

Previous work by other researchers has shown that a variety of cells (both prokaryotic and eukaryotic) will reduce external oxidants such as potassium hexacyanoferrate(III). It has also been shown that rates of hexacyanoferrate(III) reduction correlate well with oxygen uptake rates in batch cultures. None of these reports examine the effects of antibiotic or cytotoxic drugs on mediated respiratory rate measurements.

This invention presents rapid methods for evaluating the effects of antimicrobial compounds on microorganisms based upon the microorganism's ability to transport electrons to an external chemical oxidant (a mediator) that is added to the microorganism sample. The mediator interacts with the terminal components of the respiratory pathway and the extent of its consumption is related to the ability of the microorganism to respire. However, under the assay conditions described herein the extent of mediator consumption is different from the microorganisms' ability to consume oxygen, due to the addition of metabolizable compounds to the assay mixtures. The consumed mediator is subsequently measured electrochemically (amperometrically or coulometrically) at the working electrode of a standard two-electrode or three-electrode electrochemical cell. The electrochemical signals (change of current or charge with time) obtained with microorganism suspensions incubated in the absence and presence of antimicrobial compounds are significantly different. These signal differences can be used to screen for antimicrobial effectiveness of antibiotic drugs against clinically important multi-drug-resistant organisms, to screen for the presence of unlawful levels of antibiotic compounds in foodstuffs, or to screen potential new antimicrobial compounds for effectiveness against different species of microorganisms.

The following examples describe the invention in detail:

EXAMPLE 1

Screening of Fourteen Antibiotic Compounds for Effectiveness on *E. coli* JM105.

In this example, the assay uses the following steps: (1) incubation of a known quantity of microorganisms with antibiotic (sample A) and without antibiotic (sample B) for a fixed time (e.g. 15 min) and at a fixed temperature (e.g. 37° C.); (2) addition of the incubated sample to a solution containing the mediator in a standard, 3-electrode electrochemical cell; and (3) measurement of current at a fixed applied voltage (e.g. +0.5 V vs Ag/AgCl) for a fixed time (e.g 8 min). In its present configuration, our assay uses a rotating platinum disk working electrode with a surface area of approximately 0.1 cm$^2$. The current measured at this electrode is caused by the conversion of the reduced form of the mediator to its original, oxidized form at the electrode surface, while electrons are consumed by the electrode to generate the measured current. The magnitude of the measured current indicates the quantity of reduced mediator present in the assay solution. Typically, the magnitude of the current increases with time because microorganisms continually increase the concentration of reduced mediator in the assay solution. The rate at which the current increases indicates the respiration rate of the microorganisms, and conversion requires knowledge only of the total quantity of microorganisms present (which is measured as bacterial dry matter in grams/liter), and the relationship between current and reduced mediator concentration. Both of these values are easily measured. An example of the assay, and results with 14 antibiotics, are given below.

*E. coil* JM105 was grown in a sterile medium consisting of 0.144 g $KH_2PO_4$, 0.288 g $K_2HPO_4$, 0.120 g tryptone, 0.060 g yeast extract, 0.060 g sodium citrate, 0.024 g magnesium sulfate heptahydrate, 0.0024 g calcium chloride, 0.082 g ammonium sulfate, 0.067 g ammonium chloride, 40 mM glucose and 12 microliters of trace element solution dissolved in 50 mL of distilled water. The stock trace element solution consisted of 20 g iron(II) sulfate heptahydrate, 5 g manganese sulfate monohydrate, 5 g aluminum chloride hexahydrate, 2 g cobalt(II) chloride hexahydrate, 1 g zinc sulfate heptahydrate, 1 g disodium molybdate dihydrate, 0.5 g copper chloride dihydrate, and 0.25 g $H_3BO_3$ dissolved in 500 mL of 5 M hydrochloric acid. After inoculation of the medium with 1 mL of a frozen (−80° C.) stock culture of 1:1 *E. coli* JM105: glycerol, growth occurred in an incubator-shaker at 37° C. and 200 rpm. Growth was monitored by periodically measuring optical density at 600 nm. Exponential-phase cells were harvested when $OD_{600}$ values between 2 and 3 were obtained (usually after 4–5 h). Stationary phase cells were harvested after overnight cultivation (10 h). Prior to use in the drug susceptibility assay, cell growth was stopped by cooling the culture flask for a minimum of 15 min in an ice-bath. Cells prepared in this manner yielded stable and reproducible respiration rate values for 4 h, after which the values began to decrease.

Aliquots of exponential or stationary phase *E. coli* JM 105 (1.00 mL) are transferred to Eppendorf tubes and centrifuged at 12,000×g for 1.0 min. The pellet is resuspended by vortexing in 1.0 mL of buffer (growth medium including 10 mM succinate, without glucose, protein or trace elements) with or without antibiotic and incubated at 37° C. for 15.0 min. During this time, the electrochemical cell is filled with 40.0 mL of 25 mM potassium hexacyanoferrate dissolved in the same buffer. Electrodes (Pt disk working electrode, rotated at 600 rpm, Ag/AgCl reference electrode and stainless steel auxiliary electrode) are inserted into the solution, and the applied potential is set to +0.500 V. After the 15 min incubation time, the cell suspension is added to the electrochemical cell. Data obtained for cells incubated in the absence and presence of 5.1 mM tetracycline are shown in FIG. 1.

Control experiments were done by the standard agar plate method for comparison. In these experiments, filter paper disks were swelled in the antibiotic solution and placed on the surface of a prepared agar plate. *E. coli* JM105 (1.0 mL of an exponential-phase culture) was distributed over the surface of the plate. The plate was then incubated at 37° C. for 24 hours. Susceptibility to the drug was indicated by a region with no *E. coli* growth surrounding the filter paper disk.

Table 1 shows results obtained for 14 known antibiotics with this strain of *E. coli*, using the new electrochemical assay and the standard agar plate method. These antibiotics represent a spectrum of known activities and mechanisms of action. The first five (penicillin G, D-cycloserine, vancomycin, bacitracin and cephalosporin C) are known to act on the cell wall. The next four (tetracyline, erythromycin, chloramphenicol and streptomycin) inhibit protein synthesis. The next three (nalidixic acid, rifampicin and trimethoprim) inhibit nucleic acid synthesis and/or replication. The last two (amphotericin and nystatin) act on the cell membrane of certain fungi that possess a steroid of the proper configuration, like cholesterol, in the membrane. The spectrum of known activities of these antibiotics is also varied. Certain of them are generally active with gram-positive species (e.g. bacitracin, erythromycin), while others are generally active with both gram-positive and gram-negative species (e.g. penicillin G, D-cycloserine, tetracycline, chloramphenicol).

Comparison of the results of the electrochemical assay, which takes less than 30 min to perform, with the standard agar plate method, which requires 24 hours, yields an excellent correlation. We found that exponential phase cultures of *E. coli* generally showed larger responses to antibiotics in the new respiratory assay, and these results were compared with the agar plate results. In all cases in which decreased respiratory activity is measured by the new assay (seven of the fourteen antibiotics), growth inhibition was observed by the agar plate method. In one case (nalidixic acid), the agar plate method showed growth inhibition while no decrease in respiratory behavior was observed in the new assay. The remaining six antibiotics showed neither decreased respiratory behavior nor growth inhibition on agar plates.

We thus define a true positive measurement as decreased respiration (new assay) with inhibited growth (agar plate), a false positive as decreased respiration with no inhibition, a true negative as unchanged or increased respiration with no inhibition, and a false negative as unchanged or increased respiration with inhibited growth. Results obtained under these conditions, using 90% as the cutoff value for a real decrease in measured respiration, yields true positives=7, false positives=0, true negatives=5, and false negatives=2.

The results shown in Table 1 were obtained with one common strain of *E. coli*. We have also shown that mediated respiration measurements of this type can also be made with eukaryotic organisms (we have tested *S. cerevisiae*), with only a small modification of the procedure, the addition of a low concentration (5–10 $\mu$M) of a hydrophobic mediator compound like 2,6-dichlorophenol-indophenol to the hexacyanoferrate(III) assay solution.

TABLE 1

Comparison of Standard Agar Plate Results with Chronoamperometric Respiration Assay Results for *E. coli* JM105 and 14 Antibiotic Compounds

| Antibiotic | Concentration (Final, $\mu$M) | Results with Agar Plate | New Assay: Percent Activity vs. Blank | |
|---|---|---|---|---|
| | | | Exponential Phase | Stationary Phase |
| Penicillin G | 122 | Inhibition | 67 | 66 |
| D-Cycloserine | 127 | Inhibition | 56 | 76 |
| Vancomycin | 122 | Inhibition | 54 | 39 |
| Bacitracin | 123 | Growth | 170 | 190 |
| Cephalosporin C | 24 | Inhibition | 68 | 40 |
| Tetracycline | 125 | Inhibition | 22 | 50 |
| Erythromycin | 121 | Growth | 110 | 97 |
| Chloramphenicol | 121 | Inhibition | 47 | 39 |
| Streptomycin | 122 | Growth | 91 | 100 |
| Nalidixic Acid | 26 | Inhibition | 310 | 210 |
| Rifampicin | 12 | Growth | 100 | 110 |
| Trimethoprim | 61 | Inhibition | 90 | 170 |
| Amphotericin | 2 | Growth | 190 | 200 |
| Nystatin | 8 | Growth | 92 | 100 |

EXAMPLE 2

Chronocoulometric Measurement of Antibiotic Susceptibility with *E. coli*.

In this example, both volume and duration of the susceptibility test have been reduced. The procedure involves combining 20 μL of the bacterial culture with 130 μL of buffer (that contains or does not contain the antibiotic) in an Eppendorf tube, and then 150 μL of 0.1 M potassium ferricyanide solution is added. This solution is incubated for 10 min at 37 C, except in the cases of vancomycin and trimethoprim, where the incubation at 37 C was allowed to continue for 20 min. At this time, a platinum disk working electrode, Ag/AgCl reference electrode and a stainless steel auxiliary electrode are inserted, and a potential of +0.50 V is applied using a potentiostat. The measured current is integrated over time to produce a plot of total charge against time. The change in total charge is measured between 60 and 120 seconds after the potential is applied.

Table 2 shows the results of these experiments. It should be noted that these results were obtained with higher antibiotic concentrations and with significantly shorter assay times than the method and results shown in Example 1.

Again we define a true positive as growth inhibition on agar plus decreased respiration, a true negative as growth on agar plus unchanged or increased respiration, a false positive as growth on agar plus decreased respiration, and a false negative as growth inhibition on agar plus unchanged or increased respiration. Because of scatter in individual measurements, we consider an activity measurement below 90% to represent a real decrease in the mediated electrochemical respiration rate value. Under these conditions, using the data in Table 2, the following numbers are obtained: true positives=9, true negatives=4, false positives=0, and false negatives=0.

EXAMPLE 3

Effect of Lysozyme and EDTA on Electrochemical Assay Results with *E. coli*.

In this example, the effects of lysozyme and EDTA on mediated electrochemical respiration measurements were studied. Lysozyme is an enzyme that destroys cell walls and is used extensively in protein purification procedures. Ethylenediaminetetraacetate (EDTA) is a chelating agent that strongly binds calcium and magnesium ions and permeabilizes the outer membrane of *E. coli*.

*E. coli* JM105 was grown in the same manner as in Example 1. The assay procedure used to determine the effect of lysozyme on mediated electrochemical respiration rate was as follows. The bacterial suspension (20 μL) was added to 10 μL of either a blank buffer solution or a lysozyme solution (1.5 mg/mL) and these samples were incubated at 0 C for 15 min. Ferricyanide solution (270 μL) was then added so that the final ferricyanide concentration was 50 mM. These solutions were incubated at 37 C for 10 min.

Each sample was then analyzed electrochemically using a Pt working electrode, Ag/AgCl reference electrode and a stainless steel auxilliary electrode, with an applied potential of +0.500 V. The current measured at the working electrode was integrated over the time between 60 and 120 seconds. These experiments were repeated to determine average values of integrated current (charge). Results are shown in Table 3, below.

These results clearly show a significant decrease in respiration (charge) as a result of cell exposure to lysozyme. As lysozyme breaks, or lyses the cell membranes, substrates needed for enzyme reactions in the membranes that are normally trapped at high concentration inside the cells, are released into the surrounding medium and are therefore present at much lower concentrations. The lower concentrations of essential substrates is believed to be responsible for the decreased respiration measurements observed following incubation of the cells with lysozyme.

TABLE 2

Comparison of Standard Agar Plate Results with Chronocoulometric Respiration Assay Results for *E. coli* JM105 and 13 Antibiotic Compounds

| Antibiotic | Concentration (Final, μM) | Results with Agar Plate | New Assay: Percent Activity vs. Blank Exponential Phase Cells Only* |
|---|---|---|---|
| Penicillin G | 380 | Inhibition | 40 |
| D-Cycloserine | 4070 | Inhibition | 66 |
| Vancomycin | 280 | Inhibition | 75 |
| Bacitracin | 4510 | Growth | 121 |
| Cephalosporin C | 380 | Inhibition | 79 |
| Tetracycline | 2250 | Inhibition | 5 |
| Erythromycin | 880 | Growth | 102 |
| Chloramphenicol | 2860 | Inhibition | 64 |
| Streptomycin | 4030 | Growth | 90 |
| Nalidixic Acid | 375 | Inhibition | 61 |
| Rifampicin | 147 | Inhibition** | 83 |
| Trimethoprim | 1430 | Inhibition | 76 |
| Nystatin | 121 | Growth | 96 |

*Average of two measurements. Relative standard deviations (RSD) in blank samples (no antibiotic, n = 4 or 5) were always less than 6.5%. Mid- to late-exponential phase cells were used, and cultures had $OD_{600}$ values between 2.70 and 4.75.
**At this higher concentration, rifampicin inhibited *E. coli* growth. Other agar plate results obtained at these higher concentrations were identical to those obtained at the lower concentrations (see Table 1).

TABLE 3

Integrated current measurements for E. coli JM105 incubated in the absence and presence of lysozyme.

| Sample Contents | Charge ($\mu$C) | Average |
|---|---|---|
| Blank | 35.3 | 32 +/− 3 |
| Blank | 31.4 | |
| Blank | 29.6 | |
| Lysozyme | 21.6 | 22 +/− 1 |
| Lysozyme | 21.1 | |
| Lysozyme | 22.8 | |

The effect of ethylenediaminetetraacetate (EDTA) on electrochemical response was investigated in a similar manner. However, in this case, 20 $\mu$L of bacterial suspension was added to 280 $\mu$L of 50 mM ferricyanide solution that had been prepared in either the absence or presence of 5 mM EDTA. The samples were incubated 10 min at 37 C, and the electrochemical analysis was done as described above for lysozyme. Again, results are presented as the charge consumed at the working electrode between 60 and 120 seconds after the initial application of +0.500 V to the working electrode. Results are given in Table 4, below.

The increased electrochemical signals obtained for samples incubated with EDTA are explained by the higher permeability of the outer membrane of the microorganism. The greater permeability allows easier access of the ferricyanide to the redox-active species in the inner membrane, or cell wall, of the E. Coli, and thus increases the overall rate of ferricyanide reduction by the cells.

TABLE 4

Integrated current measurements for E. coli JM105 incubated in the absence and presence of EDTA

| Sample | Charge ($\mu$C) | Average |
|---|---|---|
| Blank | 40.6 | 38 +/− 2 |
| Blank | 38.3 | |
| Blank | 37.7 | |
| Blank | 37.1 | |
| EDTA | 46.3 | 45 +/− 2 |
| EDTA | 43.1 | |
| EDTA | 45.2 | |
| EDTA | 43.3 | |

EXAMPLE 4

Effect of Antibiotic Concentration on Electrochemical Assay Results

The same procedures for E. coli growth, incubation with ferricyanide and antibiotic, and measurement were used in this Example as were used in Example 2. One antibiotic was studied for the effect of concentration, and this was chloramphenicol. The final concentration of chloramphenicol and the percent chronocoulometric respiratory activity remaining are given in Table 5. Values obtained in the absence of chloramphenicol were measured as blanks, and are defined as 100% activity.

TABLE 5

Variation in Mediated Chronocoulometric Respiration Values for E. coli as a Function of Chloramphenicol Concentration.

| Chloramphenicol Concentration, $\mu$M | Mediated Chronocoulometric Respiration Activity Remaining, Percent |
|---|---|
| 0.0048 | 95 |
| 0.048 | 102 |
| 0.48 | 66 |
| 4.8 | 58 |
| 48 | 52 |
| 480 | 35 |
| 4800 | 5 |

These results clearly show a decrease in measured respiratory activity as a function of chloramphenicol concentration, as expected for an effective antibiotic compound. From these results, the minimum inhibitory concentration of chloramphenicol for E. coli JM105 is 0.48 $\mu$M, and an IC50 value of 48 $\mu$M is obtained.

EXAMPLE 5

Effect of Chloramphenicol and Lysozyme on Mediated Electrochemical Respiration Assay using Clostridium sporogenes (ATCC 8075).

This organism was chosen as a typical gram-positive, obligate anaerobe. Growth under anaerobic conditions was accomplished using a similar medium to that used for E. coli except that the concentrations of yeast extract and tryptone were doubled and the concentration of glucose was five-fold lower for the C. sporogenes growth. Assay conditions were the same as in Example 2, with the following exceptions. The incubation of 20 $\mu$L of the bacterial suspension with 130 $\mu$L of either the blank buffer or the chloramphenicol or lysozyme solution was done for 20 min at 37 C. Mediator solution (150 $\mu$L) containing 0.10 M ferricyanide and 10 $\mu$M 2,6-dichlorophenolindophenol (DCIP) was then added and the mixture was allowed to incubate for another 20 min at 37 C, giving final concentrations of 0.050 M ferricyanide and 5 $\mu$M DCIP, respectively. All manipulations were performed under a stream of nitrogen, to ensure the absence of oxygen, which is known to inhibit the growth of C. sporogenes. Measurement by chronocoulometry was performed in an identical manner as in Example 2. Table 6 shows the results of these measurements.

TABLE 6

Mediated Electrochemical Respiration Measurements on C. sporogenes, in the Absence and Presence of Chloramphenicol and Lysozyme.

| Test Compound | Final Concentration | Mediated Chronocoulometric Respiratory Activity Remaining, Percent* |
|---|---|---|
| Chloramphenicol | 5.00 mM | 24 |
| Lysozyme | 0.57 mg/mL | 80 |

*Average of two measurements. Six control (blank) solutions yielded an average integrated current (charge) value between 60 and 120 seconds of 18.5 ± 1.4 $\mu$C, and this was taken as 100% activity.

Chloramphenicol is known to be active against the growth of this strain of Clostridium (see Bergey), thus the much lower respiratory activity measured with the new electrochemical assay is expected. Lysozyme had a similar effect on C. sporogenes as it did on E. coli, with a 20% loss of activity in this Example, compared to a 31% loss of activity in E. coli under the conditions described in Example 3.

The above examples are illustrative only. It is not intended that the invention be limited to the above examples. Many variations will be apparent to those who are knowledgeable in the field, and such variations are within the scope of the invention as described and claimed, whether or not expressly mentioned herein.

What is claimed is:

1. A method of rapidly assessing susceptibility of a microorganism to a drug selected from the group consisting of an antibiotic and a cytotoxic compound, said method comprising the steps of:

obtaining a test sample of a microorganism;

arresting growth of the microorganism in the test sample;

adding a mediator to a test sample of said microorganism in the presence of said drug; said mediator being reducible by accepting an electron arising from respiration of the microorganism;

determining variation of the respiration rate of the microorganism over time by electrochemical measurement of mediator reduction in the test sample resulting from microorganism respiration, said variation of the respiration rate being observable over a time period of up to 500 seconds; and comparing variation of the respiration rate of the test sample with variation of the respiration rate in a control sample of the microorganism not exposed to said drug, thereby assessing susceptibility of the microorganism to the drug.

2. A method as recited in claim 1, wherein the step of adding a mediator to a test sample comprises:

preparing the test sample by combining a cell culture or suspension of the microorganism with a solution of the drug, the combination then being incubated for a fixed time prior to adding the mediator.

3. A method as recited in claim 2, where said mediator comprises at least one compound selected from the group consisting of: ferricyanide (hexacyanoferrate (III)); dichlorophenol-indophenol (DCIP); ferrocene and ferrocene derivatives; methylene blue; janus green; tris(bipyridyl)iron (III); a quinone; and a phenazine.

4. A method as recited in claim 2, where said drug is selected from the group consisting of:

Penicillin G;
    D-Cycloserine;
    Vancomycin;
    Bacitracin;
    Cephalosporin C;
    Tetracycline;
    Erythromycin;
    Chloramphenicol;
    Streptomycin;
    Nalidixic Acid;
    Rifampicin;
    Trimethoprim;
    Amphotericin;
    Nystatin;
    EDTA; and
    Lysozyme.

5. A method as recited in claim 1, wherein the step of adding a mediator to a test sample comprises:

preparing the test sample by combining a cell culture or suspension of the microorganism with a mediator and a solution of the drug, the combination then being incubated for a fixed time.

6. A method as recited in claim 5, where said mediator comprises at least one compound selected from the group consisting of: ferricyanide (hexacyanoferrate (III)); dichlorophenol-indophenol (DCIP); ferrocene and ferrocene derivatives; methylene blue; janus green; tris(bipyridyl)iron (III); a quinone; and a phenazine.

7. A method as recited in claim 5, where said drug is selected from the group consisting of:

Penicillin G;
    D-Cycloserine;
    Vancomycin;
    Bacitracin;
    Cephalosporin C;
    Tetracycline;
    Erythromycin;
    Chloramphenicol;
    Streptomycin;
    Nalidixic Acid;
    Rifampicin;
    Trimethoprim;
    Amphotericin;
    Nystatin;
    EDTA; and
    Lysozyme.

8. A method as recited in claim 1, where said mediator comprises at least one compound selected from the group consisting of: ferricyanide (hexacyanoferrate (III)); dichlorophenol-indophenol (DCIP); ferrocene and ferrocene derivatives; methylene blue; janus green; tris(bipyridyl)iron (III); a quinone; and a phenazine.

9. A method as recited in claim 8, wherein said quinone is selected from the group consisting of benzoquinone, naphthoquinone, menadione, anthraquinone, and substituted derivatives of these.

10. A method as recited in claim 8, wherein said phenazine is selected from the group consisting of phenazine methosulfate and phenazine ethosulfate.

11. A method as recited in claim 1, where said drug is selected from the group consisting of:

Penicillin G;
    D-Cycloserine;
    Vancomycin;
    Bacitracin;
    Cephalosporin C;
    Tetracycline;
    Erythromycin;
    Chloramphenicol;
    Streptomycin;
    Nalidixic Acid;
    Rifampicin;
    Trimethoprim;
    Amphotericin;
    Nystatin;
    EDTA; and
    Lysozyme.

12. A method as recited in claim 1 wherein the variation of the respiration rate is observable over a time period of from 60 to 120 seconds.

13. A method as recited in claim 1 additionally comprising the step of incubation of the mediator with the test sample for up to 20 minutes prior to determining variation of the respiration rate of the microorganism.

14. A method as recited in claim 13 wherein incubation of the mediator with the test sample occurs for up to 10 minutes prior to determining variation of the respiration rate of the microorganism.

15. A method as recited in claim 1 wherein the mediator is reducible by accepting an electron arising from a terminal component of the respiratory pathway of the microorganism.

16. A method of rapidly assessing susceptibility of a microorganism to a drug selected from the group consisting of an antibiotic and a cytotoxic compound, said method comprising the steps of:

obtaining a test sample of a microorganism;

arresting growth of the microorganism in the test sample;

adding a mediator to a test sample of said microorganism in the presence of said drug; said mediator being reducible by accepting an electron arising from a terminal component of the respiratory pathway of the microorganism;

incubating the mediator with the test sample for up to 20 minutes;

determining variation of the respiration rate of the microorganism over a time by electrochemical measurement of mediator reduction in the test sample resulting from microorganism respiration, said variation of the respiration rate being observable over a time period of from 60 to 120 seconds; and comparing variation of the respiration rate of the test sample with variation of the respiration rate in a control sample of the microorganism not exposed to said drug, thereby assessing susceptibility of the microorganism to the drug.

* * * * *